(12) United States Patent
Roger et al.

(10) Patent No.: US 7,374,563 B2
(45) Date of Patent: May 20, 2008

(54) APPARATUS AND METHOD FOR GUIDING A SURGICAL INSTRUMENT FOR SHAPING THE END OF A BONE

(75) Inventors: Christopher Abee Roger, Waldwick, NJ (US); Scott Dale Harrington, Upper Saddle River, NJ (US); Mark Nemec, Chester, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 187 days.

(21) Appl. No.: 11/062,083

(22) Filed: Feb. 18, 2005

(65) Prior Publication Data

US 2006/0200163 A1  Sep. 7, 2006

(51) Int. Cl.
*A61B 17/58* (2006.01)

(52) U.S. Cl. ...................................... 606/88
(58) Field of Classification Search .................. 606/79, 606/82, 86–89, 130
See application file for complete search history.

(56) References Cited

U.S. PATENT DOCUMENTS

| | | |
|---|---|---|
| 4,524,766 A | 6/1985 | Petersen |
| 4,567,885 A | 2/1986 | Androphy |
| 4,759,350 A | 7/1988 | Dunn et al. |
| 4,773,407 A | 9/1988 | Petersen |
| 4,907,578 A | 3/1990 | Petersen |
| 5,454,816 A | 10/1995 | Ashby |
| 5,514,139 A * | 5/1996 | Goldstein et al. ............. 606/79 |
| 5,611,802 A * | 3/1997 | Samuelson et al. ........... 606/86 |
| 5,688,279 A | 11/1997 | McNulty et al. |
| 5,911,723 A * | 6/1999 | Ashby et al. ................. 606/88 |
| 6,077,270 A | 6/2000 | Katz |
| 6,096,082 A | 8/2000 | Stegmuller et al. |
| 6,193,723 B1 * | 2/2001 | Cripe et al. .................... 606/88 |
| 6,916,325 B2 * | 7/2005 | Kana et al. .................... 606/89 |
| 2001/0001121 A1 | 5/2001 | Lonbardo et al. |
| 2003/0018338 A1 * | 1/2003 | Axelson et al. ............... 606/89 |
| 2004/0153083 A1 | 8/2004 | Nemec et al. |

OTHER PUBLICATIONS

1989 Howmedica Annual Product Catalog, p. C44.

\* cited by examiner

*Primary Examiner*—Eduardo C. Robert
*Assistant Examiner*—Michael Araj
(74) *Attorney, Agent, or Firm*—Lerner, David, Littenberg, Krumholz & Mentlik, LLP

(57) ABSTRACT

An apparatus for guiding a surgical instrument for shaping the end of a bone includes an alignment plate which has a contact surface and is mounted with the contact surface in a plane substantially perpendicular to the physical axis of the bone and in contact with the bone. A cutting guide is mounted to the alignment plate for rotation about an axis which is substantially parallel to the mechanical axis. The cutting guide includes an instrument-receiver which maintains the surgical instrument in a cutting plane which is substantially parallel to the contact plane and at a predetermined distance from it.

31 Claims, 6 Drawing Sheets

APPARATUS AND METHOD FOR GUIDING A SURGICAL INSTRUMENT FOR SHAPING THE END OF A BONE

BACKGROUND OF THE INVENTION

Various types of operations are routinely performed today on human joints, for example the knee joint, which involve partial or total replacement of the bone end surfaces involved in the joint. For example, knee joint replacement might involve resectioning the distal femur in order to prepare it to receive a prosthetic device.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

A basic requirement for such resectioning is that the mechanical operation of the knee joint must be preserved. That is, the operation must not change the plane in which the leg pivots about the knee joint. This requirement is commonly expressed as preserving the "mechanical axis" of the leg. This mechanical axis is a straight line which passes through the center of the femur head, the center of the knee joint, and the center of the ankle.

The anatomical axis of the femur is a line which passes through the center of the shaft portion of the femur. It is a well-known practice to use the anatomical axis in order to locate the mechanical axis prior to resectioning the distal femur. This is accomplished by inserting a rod from the distal end of the femur into the intramedullary canal of the femur. Such a rod provides a close approximation of the anatomical axis.

Various types of guides have been known which mount on such an intramedullary rod and then permit a surgeon to locate the mechanical axis for distal femur resection. See for example, U.S. Pat. Nos. 4,759,350; 5,688,281; and 6,193,723. In using these known devices, the angle between the patient's mechanical axis and his femoral anatomical axis, hereafter referred to as the "femoral offset angle", is determined ahead of time, for example from an x-ray of the leg. Once the cutting guide is mounted on the intramedullary rod, the orientation of the cutting guide is adjusted in order to preserve the femoral offset angle. After the appropriate adjustment is made for the femoral offset angle, it is necessary to secure the cutting guide in position, as by pinning to the bone, before the resection can be performed. At this point resection can proceed in a cutting plane which is perpendicular to the mechanical axis.

Rather than forcing the surgeon to use the cutting guide in a fixed position, it would be desirable to permit him to move the cutting guide once its position has been established relative to the intramedullary rod, while still maintaining it in the cutting plane, so that the surgeon can position it in order to achieve maximum exposure of the bone. It would be even more desirable to permit the cutting guide to be moved relative to the bone while the cut is being made while maintaining it in the cutting plane. This would permit the surgeon to continually maintain an optimum view of the guide, the cutting tool, and the bone.

SUMMARY OF THE INVENTION

In accordance with the present invention, an apparatus for guiding a surgical instrument for shaping the end of a bone includes an alignment plate which has a contact surface and is mounted with its contact surface in a plane substantially perpendicular to the mechanical axis of the bone and in contact with the bone. A cutting guide is mounted to the alignment plate for rotation about an axis which is substantially parallel to the mechanical axis. As used herein the description of a line or axis as being "parallel to the mechanical axis" is intended to include the mechanical axis itself. The cutting guide includes an instrument-receiver which maintains the surgical instrument in a cutting plane which is substantially parallel to the contact plane and at a predetermined distance from it.

In a preferred embodiment, the alignment plate has a cylindrical projection which is substantially perpendicular to the contact plane and projects away from the bone. This projection has a bore in it which forms an angle relative to the axis of the bushing, and this angle is equal to the femoral offset angle. The alignment plate may then be mounted on an intramedullary rod with the rod extending through the bore in the cylindrical projection. After proper rotational adjustment, the axis of the cylindrical projection will coincide with the mechanical axis. The cutting guide is then mounted for rotation about the cylindrical projection. As a result of the alignment plate construction and its rotational adjustment, the cutting guide may be rotated about the cylindrical projection for the convenience of the surgeon, while the surgical instrument will always remain in the same cutting plane. The distance between that cutting plane and the contact plane corresponds to the proximal-distal depth at which the instrument will cut in the bone.

In accordance with another aspect of the invention, the instrument receiver is mounted on a carriage which is capable of movement with two degrees of freedom. In the preferred embodiment, this is achieved by mounting the carriage for translational movement towards and away from the alignment plate. The surgeon may rotate the cutting guide relative to the mechanical axis and, the carriage will simultaneously ride towards and away from the mechanical axis, remaining in constant contact with the bone. This maintains the surface-shaping instrument in the required position for shaping the bone while being simultaneously moved relative to the bone.

The present invention allows a surgeon the freedom to make the distal resection cut at any angular location about the bone. This provides a remarkable advantage over existing systems in a number ways. For example, it allows for one instrument to be used for multiple surgical techniques. For a medial approach technique, the apparatus of the invention can be positioned and pinned to the bone more medially for maximum exposure. For a lateral approach technique the apparatus of the invention can be positioned and pinned to the bone more laterally to allow for maximum exposure. If desired, the apparatus of the invention can be used dynamically to allow for ease of resection. The surgeon can move the cutting guide rotationally about the bone while resecting, more easily avoiding soft tissue impingement.

BRIEF DESCRIPTION OF THE DRAWINGS

The foregoing brief description, as well as further objects, features and advantages of the present invention will be understood more completely from the following detailed description of a presently preferred embodiment, with reference being had to the accompanying drawings, in which.

DETAILED DESCRIPTION OF THE PREFERRED EMBODIMENT

Figure 1:
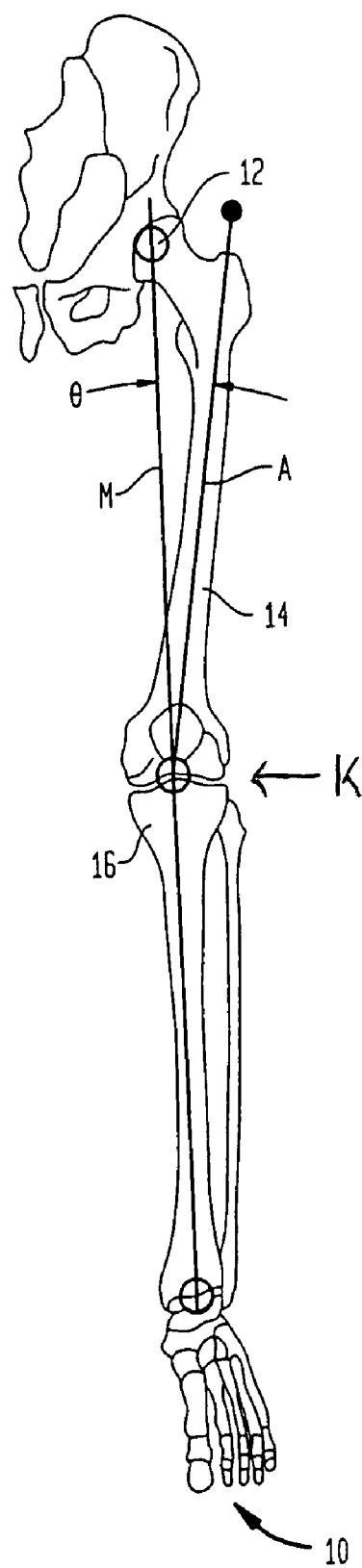
FIG. 1 is a schematic representation of a human leg providing a more detailed explanation of the mechanical and anatomical axes.

FIG. 1 is a schematic representation of the bones of a human leg and is provided to offer a more detailed explanation of the mechanical and anatomical axes. The leg 10 includes a femur 14 and a tibia 16, which cooperate at a knee joint K. The mechanical axis M is a straight line which passes through the center of the head of the femur 12, the center of the knee joint, and the center of the ankle. The anatomical axis A, on the other hand, passes through the center of the shaft portion of the femur 14. The angle θ between the anatomic axis A and mechanical axis M, the femoral offset angle. The anatomical axis A, the mechanical axis M, and the offset angle θ can all be determined by a surgeon prior to any operation from an x-ray of the patient's leg.

Figure 2:
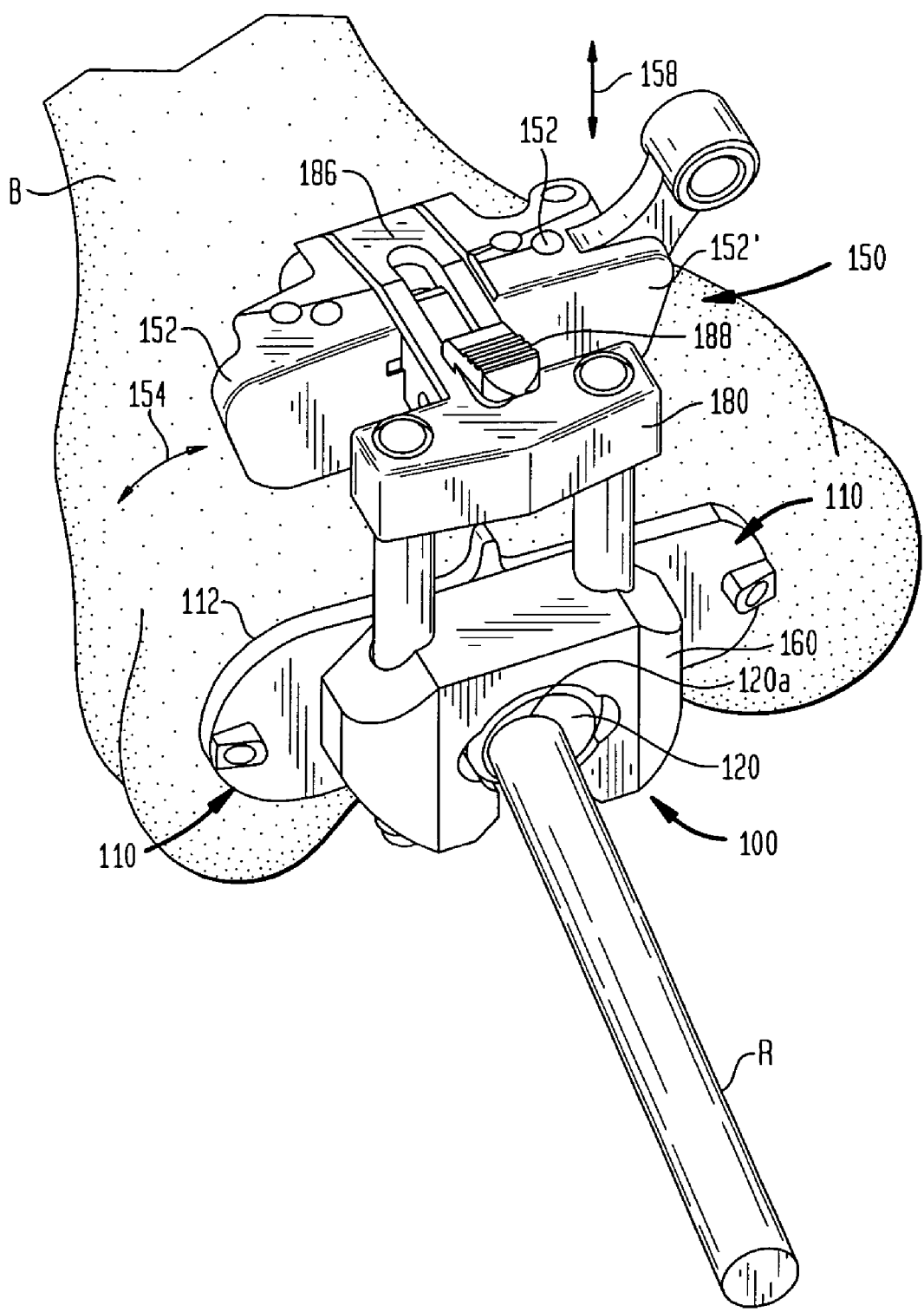
FIG. 2 is a perspective view showing the preferred embodiment of the invention assembled and in position for use.

FIG. 2 is a perspective view showing the preferred embodiment 100 of the invention assembled and ready for use by a surgeon with a surgical instrument. The apparatus 100, preferably made entirely of surgical steel, broadly comprises an alignment plate 110 which is mounted in contact with the distal end of the bone B, in this case, a femur. When properly aligned, as explained below, the plate 110 will be in contact with the femur in a plane which is perpendicular to the mechanical axis.

The alignment plate includes a cylindrical projection 120, which projects away from the bone B and is preferably concentric with the mechanical axis. Projection 120 has a bore 120a which is concentric to an axis that intersects the axis of projection 120 at an angle equal to the femoral offset angle θ. An intramedullary rod R has been inserted into the intramedullary canal of the femur from its distal end and includes a portion that projects away from the bone. As is known, this rod is coaxial with the anatomical axis. The plate 110 is mounted on the projecting portion of rod R and is rotated to an appropriate orientation as will be explained further below. When so positioned, plate 110 is then attached to the femur as will be explained further below.

A cutting guide 150 is mounted for rotation on cylindrical projection 120. Cutting guide 150 includes an instrument receiver 152 which, in use, will guide a surgical instrument such as an oscillating saw blade used to shape bone B. It will be appreciated that cutting guide 150 may be rotated clockwise or counterclockwise (in FIG. 2) relative to the cylindrical projection 120, as represented by the two-headed arrow 154. Any tool accepted by the instrument receiver would then preferably be moved in a plane perpendicular to the axis of cylindrical projection 120 (the mechanical axis) at a predetermined distance from the contact plane determined by the point at which the shaping instrument is received by the instrument receiver 152, as by being guided in contact with surface 152'. It will be appreciated that this predetermined distance corresponds to the depth of the cut made by the shaping instrument.

The instrument receiver 152 is provided on a carriage 180 which is mounted for translational movement towards and away from the cylindrical projection 120 as a result of a construction that will be discussed in further detail below. This translational movement is represented by the two-headed arrow 158. Carriage 180 may be held by the surgeon in one hand while the other hand holds the shaping instrument. Cutting guide 150 could then be rotated by moving the carriage 180 and simultaneously maintaining the instrument receiver 152 in constant contact with the bone B.

Figure 3:
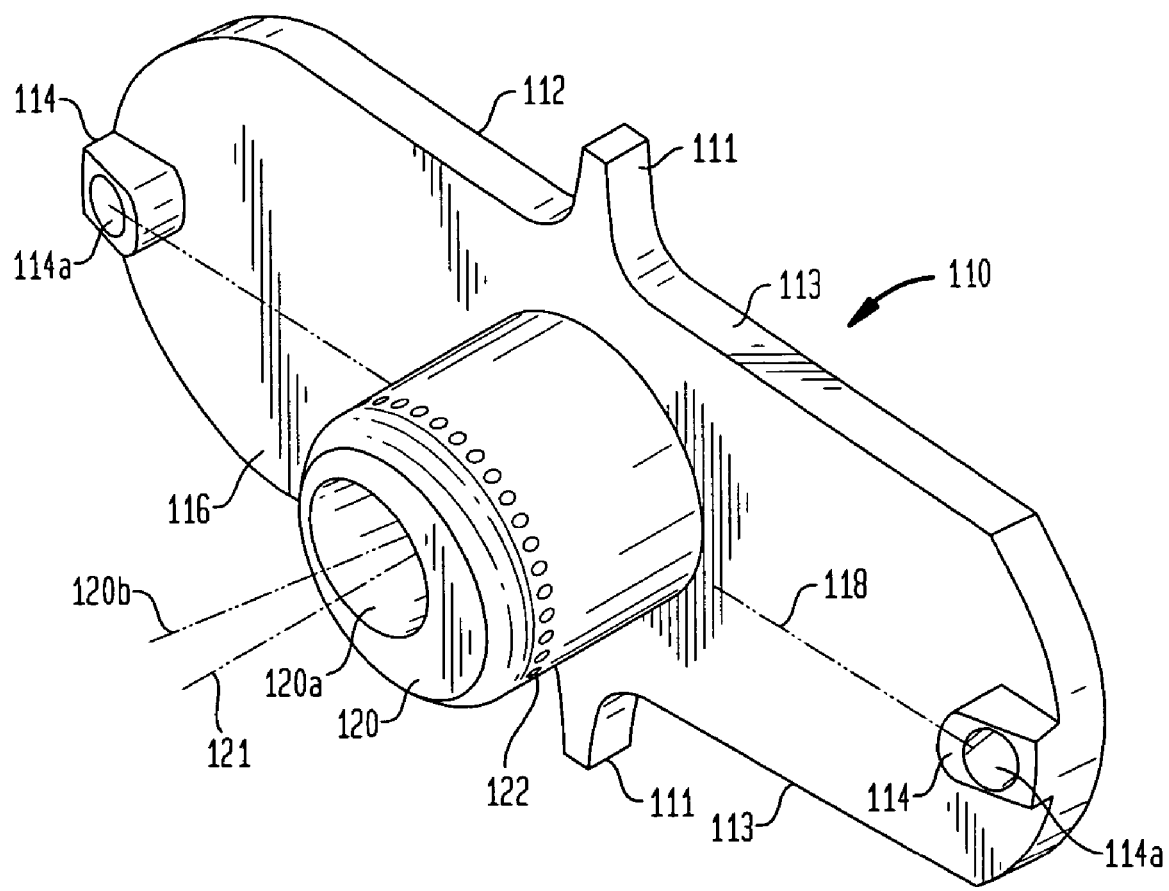
FIG. 3 is a perspective view of alignment plate 110 on an enlarged scale.

FIG. 3 is a perspective view of alignment plate 110 on an enlarged scale. The rear surface or a contact surface 112 of the plate (in FIG. 3) is flat and defines a contact plane. The front surface 116 contains a pair of oppositely located side pedestals 114, in each of which there is a through bore 114a. A line 118 extending between the axes of bores 114a, defines upper and lower halves (anterior and posterior when mounted on the femur). Upper and lower pointers 111, 111 are centered on a plane which is perpendicular to axis 118 and bisects it.

Cylindrical protrusion 120 projects outwardly (distally with respect to the distal femur) with respect to contact surface 112 and has an axis which is perpendicular to that surface. In this embodiment, that axis 121 intersects axis 118. However, the axis 121 of protrusion 120 may be spaced from axis 118. Protrusion 120 includes a cylindrical bore 120a, the axis 120b of which lies in a plane that is perpendicular to surface 112 and includes axis 118. The axis 121 of cylindrical protrusion 120 is also in this plane since it intersects axis 118. The angle between axis 120b and axis 118 is the complement of the femoral offset angle, so the angle between axis 120b and the axis 121 of cylindrical protrusion 120 will be equal to the femoral offset angle θ. Thus, when rotational alignment of alignment plate 110 brings axis 118 into the plane defined by the mechanical and anatomical axes, cylindrical protrusion 120 becomes coaxial with the mechanical axis.

In the preferred embodiment, alignment plate 110 tapers in height from left to right in FIG. 3 (in a medial direction with respect to the femur). The taper is such that the edges 113, 113 of alignment plate 110 each form an angle of 3 degrees relative to axis 118. It should be appreciated that, since alignment plate 110 is symmetrical about axis 118, it may be used on either the right or left femur by simply rotating it 180 degrees.

The alignment plate 110 can be provided in a variety of "sizes", depending upon the patient's femoral offset angle. Preferably, a set of alignment plates is provided which includes plates with different offset angles ranging from 2-9 degrees in 1 degree increments. By virtue of the described construction of the alignment plate, once the alignment plate is placed upon a rod which has been installed into the intramedullary canal by passing the rod through bore 120a, alignment plate 110 will be properly positioned with respect to the femur. It is then only necessary to align alignment plate 110 rotationally relative to the femur.

To facilitate rotational alignment of alignment plate 110, a number of guides have been built into alignment plate 110, and the surgeon has the choice of which he wishes to use. For example, the surgeon could visually center the pedestals 114, 114 on the lateral and medial epicondyles. Alternately, he could visually align the pointers 111, 111 with the "Whiteside line", which is an imaginary line extending from the femoral intercondylar groove through the center of the intercondylar fossa. As a further alternative, the surgeon could visually align the bottom edge of the alignment plate 110 so that it is parallel to a tangent to the posterior condyles. The 3 degree taper of the edges relative to the axis 118 will then assure the proper alignment of the alignment plate 110.

Once the alignment plate 110 is rotationally aligned, it can be secured in placed by inserting pins into the distal end of the femur through the bores 114a, 114a in alignment plate 110.

Figure 4:
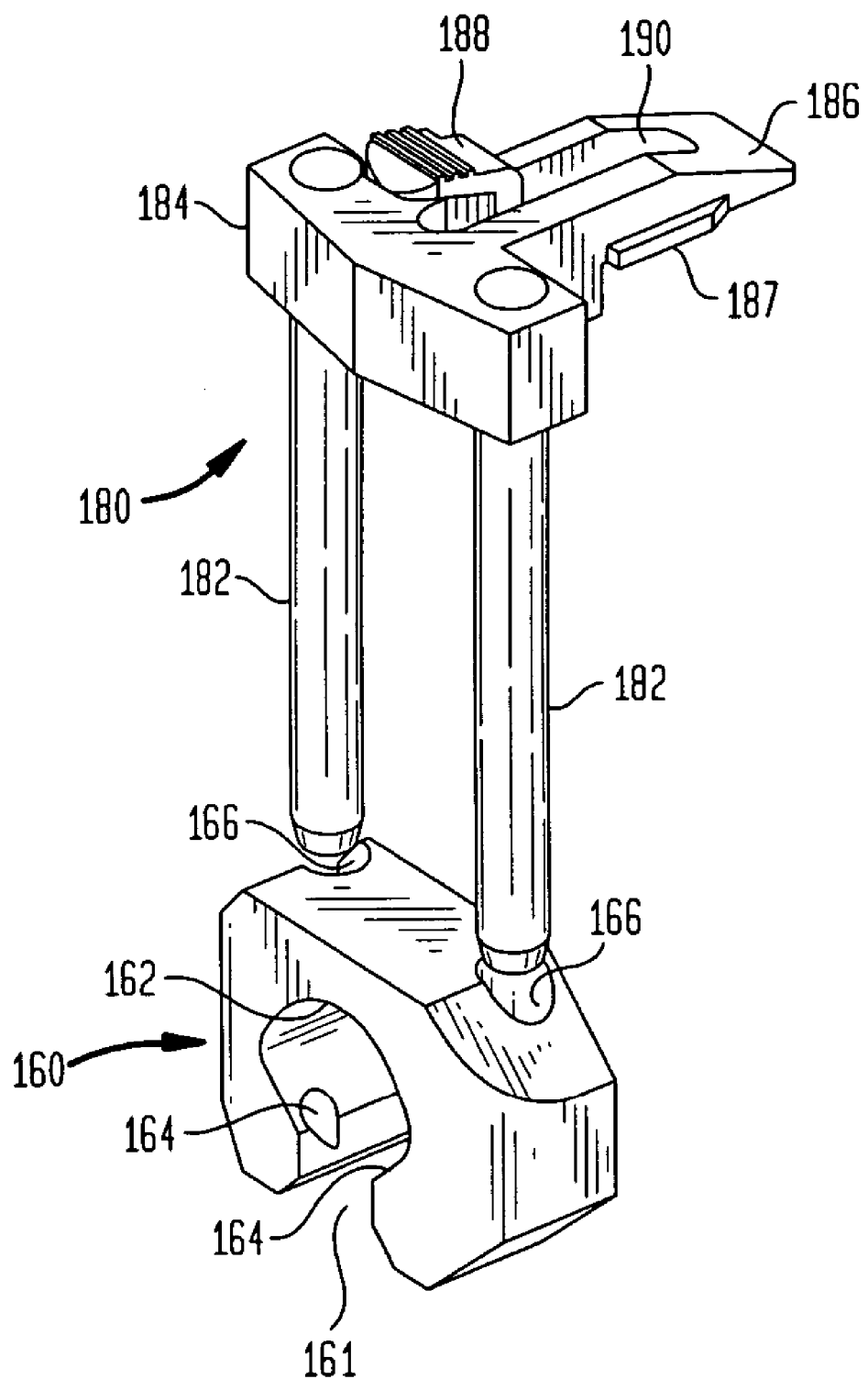
FIG. 4 is a perspective view showing two components of the cutting guide in the process of assembly.

At this point, cutting guide 150 may be mounted on the cylindrical protrusion 120. Preferably, the cutting guide is first assembled. FIG. 4 is a perspective view showing two components of the cutting guide, a bushing 160 and a carriage assembly 180, in the process of assembly.

Preferably, bushing 160 has a generally cylindrical opening which has an internal cylindrical surface 162 dimensioned to fit closely over cylindrical protrusion 120, but to slide freely thereover. Cylindrical surface 162 is interrupted by a generally axial cut-out 161, which opens downwardly to the outside of bushing 160. The radial dimension of cut-out 161 is sufficiently large to permit bushing 160 to slip over the rod R, permitting convenient mounting of bushing 160 on cylindrical protrusion 120 after alignment plate 110 has been pinned to the bone. Generally cylindrical, opposed passageways 164,164 open into surface 162 and are dimensioned to receive a spring/loaded ball bearings (not shown) which protrude into bushing bore internal surface 162. As will be understood by those skilled in the art, the ball bearings cooperate with a circumferentially arranged sequence of depressions 122 on the surface of cylindrical protrusion 120 to define a detent mechanism. Once the bushing 160 is moved sufficiently far onto the cylindrical protrusion 120, each of the ball bearings will click into one of the recesses or depressions in the series 122. Bushing 160 will then be retained securely on cylindrical protrusion 120 and may be rotated thereabout through a series of click stops, as the ball bearings are received in successive pairs of the recesses 122.

Bushing 160 also includes a pair of spaced, upright bores 166,166, which are parallel. These bores are dimensioned and located to receive carriage assembly 180. Specifically, carriage assembly 180 includes a pair of cylindrical, depending legs 182,182 which are dimensioned to be received in bores 166,166 with a close fit, but for free-sliding movement.

In the preferred embodiment, legs 182, 182 are fixedly attached to a head 184, which also includes a protruding nose 186 and a locking lever 188 mounted in an elongated cut-out 190 extending along nose 186. The nose 186 includes a spaced guide rail 187 on either side. As best seen in FIG. 2, in use, an instrument receiver 152 is mounted on nose portion 186, at which time, lever 188 locks the instrument receiver in position, as explained further below. The instrument receiver may be released by depressing lever 188.

Figure 5:
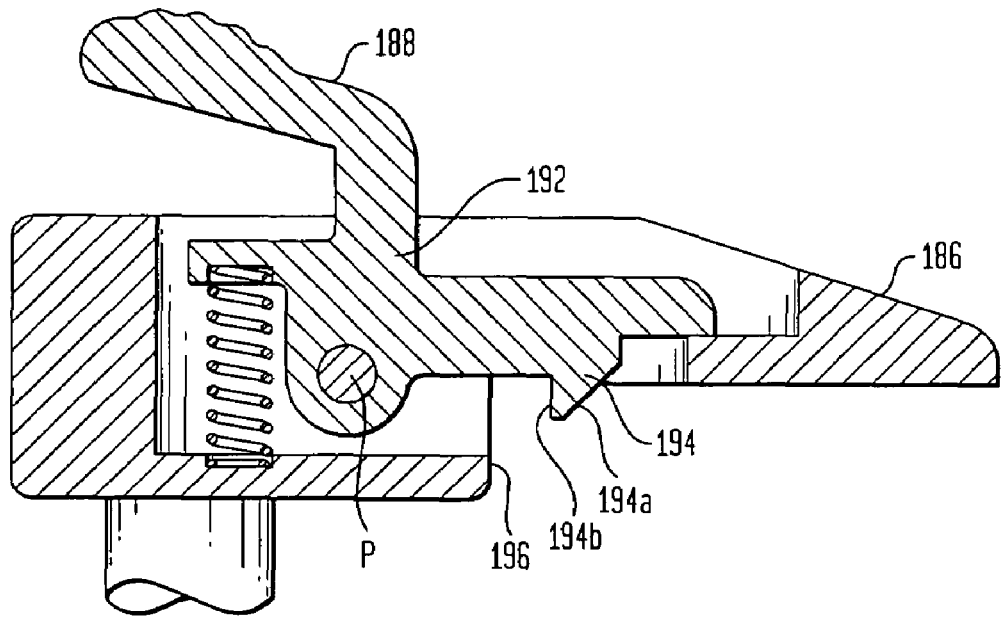
FIG. 5 is a fragmentary sectional view, on an enlarged scale, showing the upper portion of the carriage assembly.

FIG. 5 is a fragmentary sectional view of the upper portion of carriage assembly 180. The section is taken in a plane which passes between the legs 182,182 and down the center of cut-out 190. As may be seen in FIG. 5, lever 188 includes a lower, L-shaped portion 192 which has a depending hook portion 194 with a leading ramp portion 194a which terminates in a vertical face 194b. Lever 188 is mounted for pivotal movement at P and is spring loaded in the position shown in FIG. 5. When an instrument receiver 152 is placed on the nose 186 and pressed towards the left in FIG. 5, it will eventually engage ramp portion 194a and force lever 188 to rotate counterclockwise against its spring loading. Assuming a wall of instrument receiver 152 engages ramp 194a, when that wall clears face 194b, the spring loading of lever 188 forces it to rotate clockwise, capturing the wall 158 of instrument receiver 152. The instrument receiver can then be released only by depressing lever 188.

Carriage assembly 180 has a wall 196 which is located at a predetermined distance from legs 182, 182. This distance is calculated to place the instrument receiver at a predetermined distance from legs 182, 182 and, therefore, at a predetermined distance from contact surface 112 of alignment plate 110. In the preferred embodiment, instrument receiver 152 has a guide surface 152' which the surgeon uses to guide the surgical instrument in use. The location of wall 196 places that surface at a predetermined distance from the contact plane of alignment plate 110. When a distal femur resection is being performed, this distance determines the depth of the cut or material being removed from the bone.

In the preferred embodiment, three different carriage assemblies 180 are provided which provide resection depths of 8 mm, 10 mm and 12 mm, respectively. Those skilled in the art will appreciate that it would also be possible to provide a carriage assembly in which the distance of wall 196 from legs 182, 182 is adjustable, so that a continuous adjustment of resection depth is provided. Those skilled in the art will also appreciate that, alternatively, a single size of carriage assembly could be provided, and the depth adjustment could, instead, be provided on different, interchangeable instrument receivers.

Figure 6:
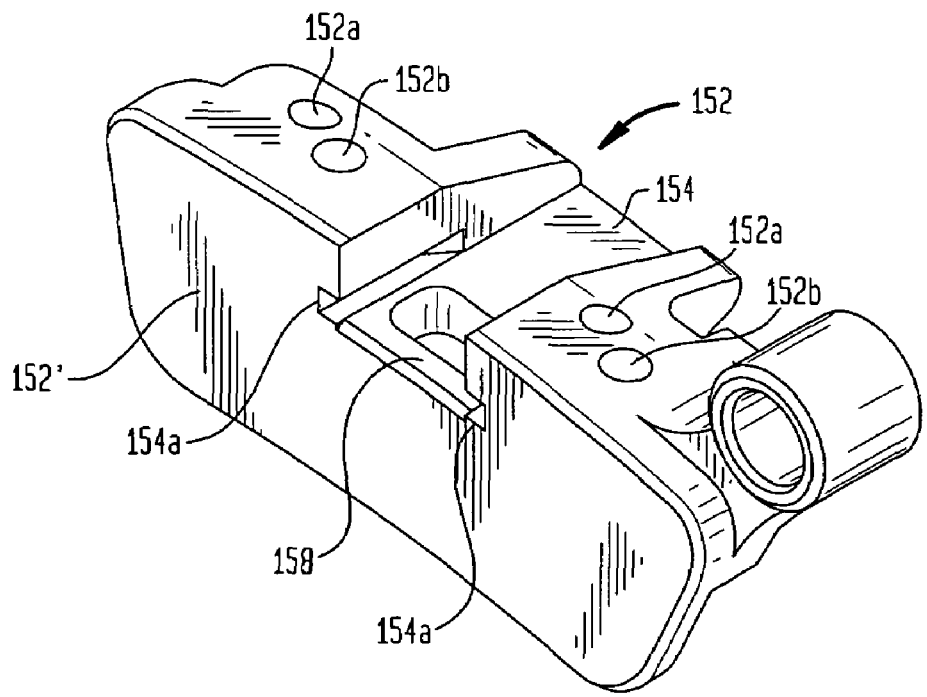
FIG. 6 is a perspective view of instrument receiver 152 on an enlarged scale.

FIG. 6 is a perspective view of instrument receiver 152 which guides a surgical instrument during resection. The instrument receiver broadly comprises a mounting channel 154 and an instrument guide face 152'. Channel 154 is dimensioned to receive the nose 186 of carriage assembly 180. Lateral grooves 154a, 154a are provided in channel 154 to receive rails 187,187 of nose 186. As may be seen, channels 154a, 154a conform to rails 187,187 so as to assure the position of instrument receiver 152 on nose 186. The bottom of channel 154 is provided with an opening to form a rear wall 158. Wall 158 cooperates with hook portion 194 of lever 188 to lock instrument receiver 152 on nose portion 186, as explained previously. Wall 158 is dimensioned so that face 194b of hook portion 194 just clears the wall when instrument receiver 152 is full seated on nose 186.

Instrument receiver 152 includes two pairs of through holes 152a, 152a and 152b, 152b. This permits instrument receiver 152 to be used in a conventional manner, which involves securing instrument receiver 152 at the distal end of the bone by passing pins into the bone through a pair of the apertures. In use, once guide 152 is pinned in position by inserting pins in the distal femur, the remaining components of instrument 100 may then be removed, and resection may proceed in a conventional manner. However, even in this mode of use, the present invention provides a significant advantage. Apparatus 100 positions guiding face 152' in the precise plane of the cut to be made, and it remains within that plane regardless of the rotational position of apparatus 100. At the same time, carriage assembly 180 moves freely with respect to the distal end of the bone, even after instrument 100 is secured to the femur by pinning alignment plate 110, and instrument receiver 152 always remains in contact with the femur as it is moved. The surgeon may therefore pin instrument receiver 152 at any rotational position on the femur and can be assured that the resection will always be made in the proper plane. This permits the surgeon to position instrument receiver 152 so as to obtain the optimal exposure of the bone.

On the other hand, apparatus 100 may be used in a mode which is not available with known instruments. That is, after alignment plate 110 is pinned, the surgeon may hold instrument receiver 152 in one hand while guiding the surface-shaping instrument against surface 152' with the other hand. He may then move instrument carrier 152 freely while he is performing the cut, yet he will always be assured that the cut is being made in the proper plane.

After the distal cut is made on the femur, it may be used as a reference to make the remaining cuts (anterior, posterior, posterior chamfer and anterior chamfer cuts) on the femur to receive a typical femoral component. The steps to be performed in a typical knee joint replacement procedure are disclosed in U.S. Pat. No. 4,524,766, the disclosure of which is incorporated herein by reference.

Figure 7:
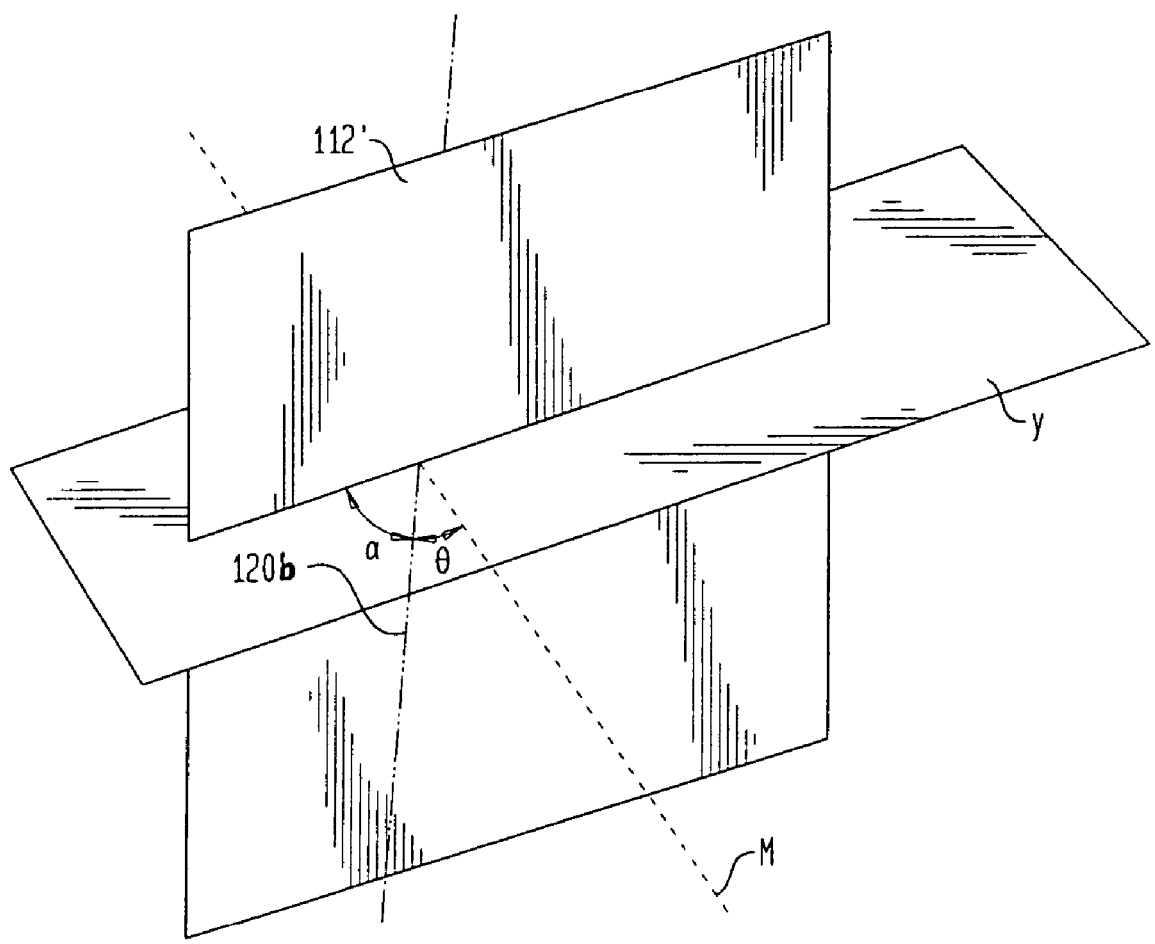
FIG. 7 is a schematic diagram illustrating the geometry of the apparatus of the invention.

Consideration of the geometric aspects of the preferred embodiment will offer insight into the structure of the invention. FIG. 7 is a schematic diagram illustrating the geometry of apparatus 100. The axis 120b of bore 120a, intersects the plane 112' of face 112. By design, the angle $\alpha$ between plane 112' and axis 120b is the complement of the femoral offset angle $\theta$. The angle of axis 120b relative to plane 112' is measured in a plane y which contains line 120b and is perpendicular to plane 112'. Reference line 118 in FIG. 3 could be thought of as an edge view of plane y, and is shown in FIG. 7 as the intersection between planes 112a' and y.

In the preferred embodiment, cutting guide 150 is mounted for rotation about an axis which is perpendicular to plane 112' and it is also moveable towards and away from its axis of rotation. As a result, cutting guide 150 exhibits planar movement with two degrees of freedom. This is inherently a polar coordinate system defined by the rotational position of the surgical instrument and its distance from the axis of rotation. This is a particularly effective construction allowing a compact instrument. Those skilled in the art will appreciate that there are many alternate ways to achieve two degrees of freedom, including translational arrangements defining a Cartesian coordinate system (e.g. a sliding carriage on orthogonal guides) in the plane of movement of the surgical tool.

In the preferred embodiment, when alignment plate 110 is mounted on rod R, axis 120b is brought into coincidence with the anatomical axis A. The rotational alignment procedure for alignment plate 110 is designed to place the mechanical axis M in plane y. Therefore the angle in plane y between axis 120b and the mechanical axis M is equal to $\theta$ (the femoral offset angle). Since the angle between axis 120b and plane 112' is designed to be equal to $\alpha$ (the complement of the femoral offset angle) plane 112' is perpendicular to the mechanical axis, the sum of $\alpha$ and $\theta$. Cutting guide 150 rotates about an axis which is also perpendicular to plane 112' and therefore guides the surgical instrument in a plane which is perpendicular to the mechanical axis.

Although a preferred embodiment of the invention has been disclosed for illustrative purposes, those skilled in the art would appreciate that many additions, modifications, and substitutions are possible without departing from the scope and spirit of the present invention as defined in the accompanying claims.

The invention claimed is:

1. A system for guiding a surgical instrument to operate on an end of a bone of a patient, the bone defining an anatomical axis and requiring shaping along a plane which is substantially perpendicular to a predefined mechanical axis related to use of the bone in the patient's body, the apparatus comprising:

a plurality of alignment plates each having a contact surface, a cylindrical protrusion formed on the alignment plate so as to protrude away from the bone along a protrusion axis perpendicular to the contact surface, and a bore extending along a bore axis, the protrusion axis and the bore axis forming an angle, the alignment plate constructed to be mounted and affixed relative to the bone in a predefined position relative to the anatomical axis with the contact surface contacting the end of the bone in a contact plane substantially perpendicular to the mechanical axis, wherein at least two of the alignment plates have different angles; and a cutting guide adapted to be mounted on the cylindrical protrusion of said alignment plate for rotation about the protrusion axis, the cutting guide having an instrument-receiver constructed and arranged to guide the surgical instrument to shape the bone at a predetermined distance from the contact plane, this predetermined distance corresponding to depth of cut of the surgical instrument.

2. The system of claim 1, wherein the bore is substantially concentric to the anatomic axis when the alignment plate is mounted in contact with the end of the bone.

3. The system of claim 2, wherein the bore is in the cylindrical protrusion.

4. The system of claim 2, wherein the angle is the complement of an offset angle between the anatomical axis and the mechanical axis.

5. The system of claim 4, wherein the bore is dimensioned to fit on a rod which has been inserted into the bone so as to extend substantially along the anatomic axis and to protrude from the end of the bone, each alignment plate further comprising an alignment guide facilitating rotation of the guide plate about the rod to a position in which the contact plane is substantially perpendicular to the mechanical axis.

6. The system of claim 2, wherein the bore is dimensioned to fit on a rod which has been inserted into the bone so as to extend substantially along the anatomic axis and to protrude from the end of the bone, each alignment plate further comprising an alignment guide facilitating rotation of the guide plate about the rod to a position in which the contact plane is substantially perpendicular to the mechanical axis.

7. The system of claim 6, wherein the alignment guide is a visually perceptible indicator which is positioned to align visually with anatomic landmarks on the bone when the contact plane is perpendicular to the mechanical axis.

8. The system of claim 2, wherein the bore is dimensioned to fit on a rod which has been inserted into the bone so as to extend substantially along the anatomic axis and to protrude from the end of the bone, the cutting guide having a bore dimensioned to fit over the cylindrical protrusion, the cutting guide bore being interrupted by an axially coextensive cut-out opening outside of the cutting guide, the cut-out having a circumferential dimension at least as large as a diameter of the rod, whereby the cutting guide may be slipped over the rod to facilitate assembly of the cutting guide on the cylindrical protrusion after the alignment plate has been affixed relative to the bone.

9. The system of claim 1, further comprising said cutting guide including an instrument carriage mounted for translational movement relative to said alignment plate, said carriage including said instrument receiver.

10. The system of claim 1, wherein each alignment plate includes securing means for securing the alignment plate to the bone.

11. The system of claim 10, wherein the securing means include bores capable of receiving pins.

12. The system of claim 1, further comprising means for mounting said cutting guide to the cylindrical protrusion of each alignment plate.

13. The system of claim 12, wherein the means for mounting include a bushing on the cutting guide being mountable on the cylindrical protrusion for rotation thereabout.

14. The system of claim 13, wherein the means further include a circumferentially arranged sequence of depressions and at least one projection capable of cooperating with the depressions.

15. The system of claim 14, wherein the cylindrical protrusion includes the depressions and the bushing includes the projection.

16. The system of claim 15, wherein the projection is a ball bearing.

17. A system for guiding a surgical instrument to operate on an end of a patient's bone, the bone defining an anatomical axis and requiring shaping along a plane which is substantially perpendicular to a predefined mechanical axis related to the patient's use of the bone, the apparatus comprising:
  a plurality of alignment plates each having a contact surface, a cylindrical protrusion formed on the alignment plate so as to protrude away from the bone along a protrusion axis perpendicular to the contact surface, and a bore extending along a bore axis, the protrusion axis and the bore axis forming an angle, the alignment plate constructed to be mounted and affixed relative to the bone in a predefined position relative to the anatomical axis with the contact surface contacting the end of the bone in a contact plane substantially perpendicular to the mechanical axis, wherein at least two of the alignment plates have different angles;
  a cutting guide constructed and arranged to guide the surgical instrument to shape the bone at a predetermined distance from a reference location on the cutting guide; and
  means for mounting said cutting guide to the cylindrical protrusion of said alignment plate for rotation about the protrusion axis with the reference location at a predetermined distance from the contact plane.

18. The system of claim 17, wherein the means for mounting comprises bushing means on the cutting guide being mountable on the cylindrical protrusion for rotation thereabout.

19. The system of claim 18, wherein the bore is in the cylindrical protrusion.

20. The system of claim 19, wherein the angle is the complement of an offset angle between the anatomical axis and the mechanical axis.

21. The system of claim 20, wherein the bore is dimensioned to fit on a rod which has been inserted into the bone so as to extend substantially along the anatomic axis and to protrude from the end of the bone, each alignment plate further comprising an alignment guide facilitating rotation of the guide plate about the rod to a position in which the contact plane is substantially perpendicular to the mechanical axis.

22. The system of claim 18, wherein the bore is dimensioned to fit on a rod which has been inserted into the bone so as to extend substantially along the anatomic axis and to protrude from the end of the bone, the cutting guide having a bore dimensioned to fit over the cylindrical protrusion, the cutting guide bore being interrupted by an axially coextensive cut-out opening outside of the cutting guide, the cut-out having a circumferential dimension at least as large as a diameter of the rod, whereby the cutting guide may be slipped over the rod to facilitate assembly of the cutting guide on the cylindrical protrusion after the alignment plate has been affixed relative to the bone.

23. The system of claim 18, wherein the means further include a circumferentially arranged sequence of depressions and at least one projection capable of cooperating with the depressions.

24. The system of claim 23, wherein the cylindrical protrusion includes the depressions and the bushing includes the projection.

25. The system of claim 24, wherein the projection is a ball bearing.

26. The system of claim 17, wherein the bore is dimensioned to fit on a rod which has been inserted into the bone so as to extend substantially along the anatomic axis and to protrude from the end of the bone, each alignment plate further comprising an alignment guide facilitating rotation of the guide plate about the rod to a position in which the contact plane is substantially perpendicular to the mechanical axis.

27. The system of claim 26, wherein the alignment guide comprises visually perceptible indicator means which positioned to align visually with anatomic landmarks on the bone when the contact plane is perpendicular to the mechanical axis.

28. The system of claim 26, wherein the bone is the human femur and the rod extends along the intramedullary canal thereof.

29. The system of claim 17, further comprising said cutting guide including an instrument carriage mounted for translational movement relative to said alignment plate, said carriage including said instrument receiver.

30. The system of claim 17, wherein each alignment plate includes securing means for securing the alignment plate to the bone.

31. The system of claim 30, wherein the securing means include bores capable of receiving pins.

* * * * *